US00PP13025P2

(12) United States Plant Patent
Whetman

(10) Patent No.: US PP13,025 P2
(45) Date of Patent: Oct. 1, 2002

(54) DIANTHUS PLANT NAMED 'BRILLIANT STAR'

(76) Inventor: John Whetman, H. R Whetman & Son Houndspool, Ashcombe Road, Dawlish, Devon EX7 0QP (GB)

( * ) Notice: Subject to any disclaimer, the term of this patent is extended or adjusted under 35 U.S.C. 154(b) by 0 days.

(21) Appl. No.: 09/633,302

(22) Filed: Aug. 8, 2000

(51) Int. Cl.[7] ..... A01H 5/00
(52) U.S. Cl. ..... Plt./272
(58) Field of Search ..... Plt./272, 263

(56) References Cited

U.S. PATENT DOCUMENTS

PP2,478 P * 2/1965 Mittleider ..... Plt./272

OTHER PUBLICATIONS

UPOV ROM GTITM Computer Database, GTI JOUVE retrieval software 2001/02, citation for 'Brilliant Star'.*

* cited by examiner

*Primary Examiner*—Bruce R. Campell
*Assistant Examiner*—Anne Marie Grünberg

(57) ABSTRACT

A new cultivar of Dianthus named 'Brilliant Star' that is characterized by it's double white, fragrant flowers with a distinct dark magenta eye zone combined with a compact plant habit, dark green, glaucous foliage, a perpetual flowering habit and a day neutral flowering response.

2 Drawing Sheets

CROSS-REFERENCES TO RELATED APPLICATIONS

The application for this new invention will be co-pending with another application corresponding to a plant that was derived from the same breeding program; entitled Dianthus Plant Named 'Pixie Star', Ser. No. 09/633,301.

BACKGROUND OF THE INVENTION

The present invention relates to a new and distinct cultivar of Alpine Dianthus and will be referred to hereafter as 'Brilliant Star'. Alpine Dianthus are of hybrid origin and are hardy perennials grown for landscape use.

The new Dianthus resulted from a breeding program conducted by the inventor in Dawlish, Devon, England. The breeding project that resulted in the selection of the "Star Series" of Alpine Dianthus began in 1992 after growing and evaluating over 80 varieties of Dianthus. The primary focus of the breeding program is to select alpine type Dianthus in a range of unique flower colors that do not require vernalization for flowering and exhibited a compact plant habit with short flower stems. 'Brilliant Star' was selected as a single plant that resulted from crossing the cultivar 'Whatfield Cyclops' (unpatented) as the seed parent with an unnamed Dianthus plant as the pollen parent.

'Brilliant Star' was selected for it's unique flower color combined with other describe characteristics. The new variety of Dianthus can be characterized by it's double, white flowers with dark magenta centers combined with a compact plant habit, dark green, glaucous foliage, a perpetual flowering habit and a day neutral flowering response. The new invention is unlike any other Dianthus that is known to the inventor. It is similar to the co-pending variety 'Pixie Star' in its perpetual flowering habit and the ability to flower without vernalization, however differs in other characteristics including flower color. 'Brilliant Star' differs from the seed parent, 'Whatfield Cyclops' (unpatented), in having white petals with a dark eye, a more compact habit, a perpetual blooming habit and a day neutral flowering response. 'Whatfield Cyclops' (unpatented) has flowers that are bright magenta with a dark magenta eye. The new invention is most similar to the cultivar 'Spring Star' (unpatented) in overall characteristics, however, 'Brilliant Star' is more compact and 'Spring Star' (unpatented) has light magenta colored blooms.

Asexual reproduction of the new cultivar was first accomplished by taking shoot cuttings in Dawlish, Devon, England in 1997 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish this cultivar from other commercial varieties. 'Brilliant Star' has not be tested under all possible conditions and phenotypic differences may be observed with variations in environmental, climatic, and cultural conditions:

1. The flowers of 'Brilliant Star' are double and white a dark magenta eye zone.
2. 'Brilliant Star' has a compact growth habit.
3. The foliage of 'Brilliant Star' is dark green and glaucous.
4. 'Brilliant Star' is perpetual blooming.
5. 'Brilliant Star' is day neutral and does not require vernalization to initiate flowers.
6. 'Brilliant Star' is hardy at least to USDA Zone 5.

BRIEF DESCRIPTION OF THE DRAWING

The first drawing is of Dianthus 'Brilliant Star' and shows the plant and habit when in bloom.

The second drawing shows a close-up of the flowers of 'Brilliant Star'. All photographs were taken in May and are of plants grown in one-gallon containers in Encinitas, Calif. The colors in these photographs are as accurate as possible by conventional photography.

BOTANICAL DESCRIPTION OF THE PLANT

The following is a detailed description of the new cultivar as grown in a one-gallon container under greenhouse conditions in Encinitas, Calif. The observed plant had been produced from shoot cuttings taken in the previous summer to the date of observation in May 2000. The plant had been overwintered at a night minimum temperature of 65 degrees Fahrenheit with day venting at 75 degrees Fahrenheit. The greenhouse was lightly shaded to an approximate light intensity of 5000 foot-candles. Day length was as naturally occurring in Southern California, approximately 13 hours during the month prior to flowering and observation. The color determination is in accordance with The R.H.S. Colour Chart of The Royal Horticultural Society, London, England, except where general color terms of ordinary dictionary significance are used.

Botanical classification: Dianthus 'Brilliant Star' is a cultivar of Alpine Dianthus and is of hybrid origin.

Commercial classification: Hardy Perennial and container plant.

Parentage: Dianthus 'Whatfield Cyclops' (unpatented) as seed parent; unnamed Dianthus plant as pollent parent.

Plant description:

*Blooming period.*—Perpetual during the growing season. Blooms from April–October. Lastingness of the blooms: Individual blooms last from 7 days at a temperature of 70° F. to 12 days at a temperature of 50° F.

*Plant habit.*—Dense cushion form, clump-forming.

*Height and spread.*—13 cm in height and spread.

*Hardiness.*—Zone 5 (possibly 4).

*Type.*—Evergreen perennial herb.

*Root system.*—Fibrous.

*Propagation.*—Shoot cuttings.

*Culture.*—Sunny location in well-drained, moderately fertile soils.

*Disease and pests.*—No known unique susceptibility or resistance. Susceptible to known Dianthus diseases and pests.

Stems:

*Shape.*—Round.

*Size.*—1.0–1.5 mm in diameter.

*Surface.*—Glaucous.

*Color.*—137C.

*Branching.*—Numerous basal breaks.

*Internode length.*—Congested, 0.7–1.0 mm and 1.5–2.0 cm on terminal internodes before peduncles.

*Peduncles.*—2.0–3.0 cm in length, 1.0–1.5 mm in width, 137C in color.

Leaves:

*Shape.*—Lanceolate.

*Divison.*—Simple.

*Apex.*—Acute.

*Base.*—Decurrent.

*Ventation.*—Not prominent.

*Margins.*—Entire.

*Arrangement.*—Opposite.

*Surface.*—Glaucous (upper and lower surface).

*Size.*—3–5 cm in length, 2–3 mm in width.

*Color.*—Upper and lower surface; young leaves 137D, mature leaves 137A.

*Fragrance.*—None.

Flowers:

*Type.*—Salviform, single (one per stem), symmetrical.

*Size.*—2.8–3.2 cm in diameter, 2.5–3.0 cm in height (including calyx).

*Fragrance.*—Clove scented.

*Petals.*—10–14 (Double), apopetalous, overlapping.

*Size.*—1.0–1.1 cm in length, 0.4 cm (at base) to 1.3 cm in width, eye zone is 1.0 cm in width and 0.6 cm in length.

*Color* (*upper surface*).—White 155D with a light pink blush 62D, eye 59A.

*Color* (*lower surface*).—Uniform white 155D except that a shadow of the eye can be seen if the petal is viewed from below.

*Calyx.*—1 calyx with 5 synsepalous, persistent, notched lobes, glabrous surface, size; 1.6–1.8 cm in length, 0.5–0.6 cm in width, color; 143C. Epicalyx present 5 mm in height.

*Reproductive organs.*—Stamens; 10, 2 whorls, stamens of outer whorl are shorter, apostemonous, distinct, develop after pistil development (self incompatible), exserted 3 mm above corolla.

*Pistil.*—1, 2 stigmas, style color white, protruding 1.0–1.2 cm above petals, ovary is superior.

I claim:

1. A new and distinct cultivar of Dianthus plant named 'Brilliant Star' as described and illustrated.

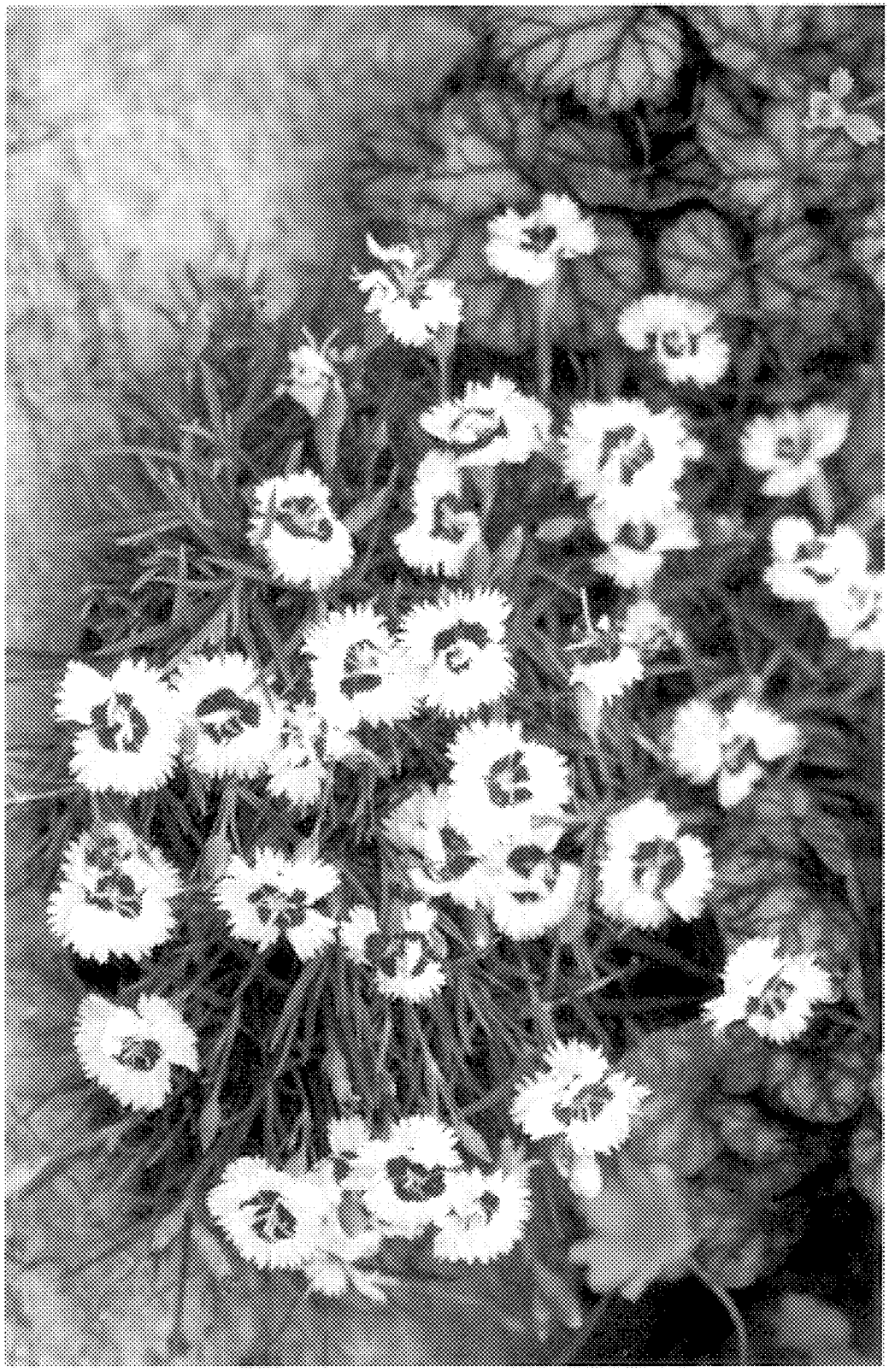

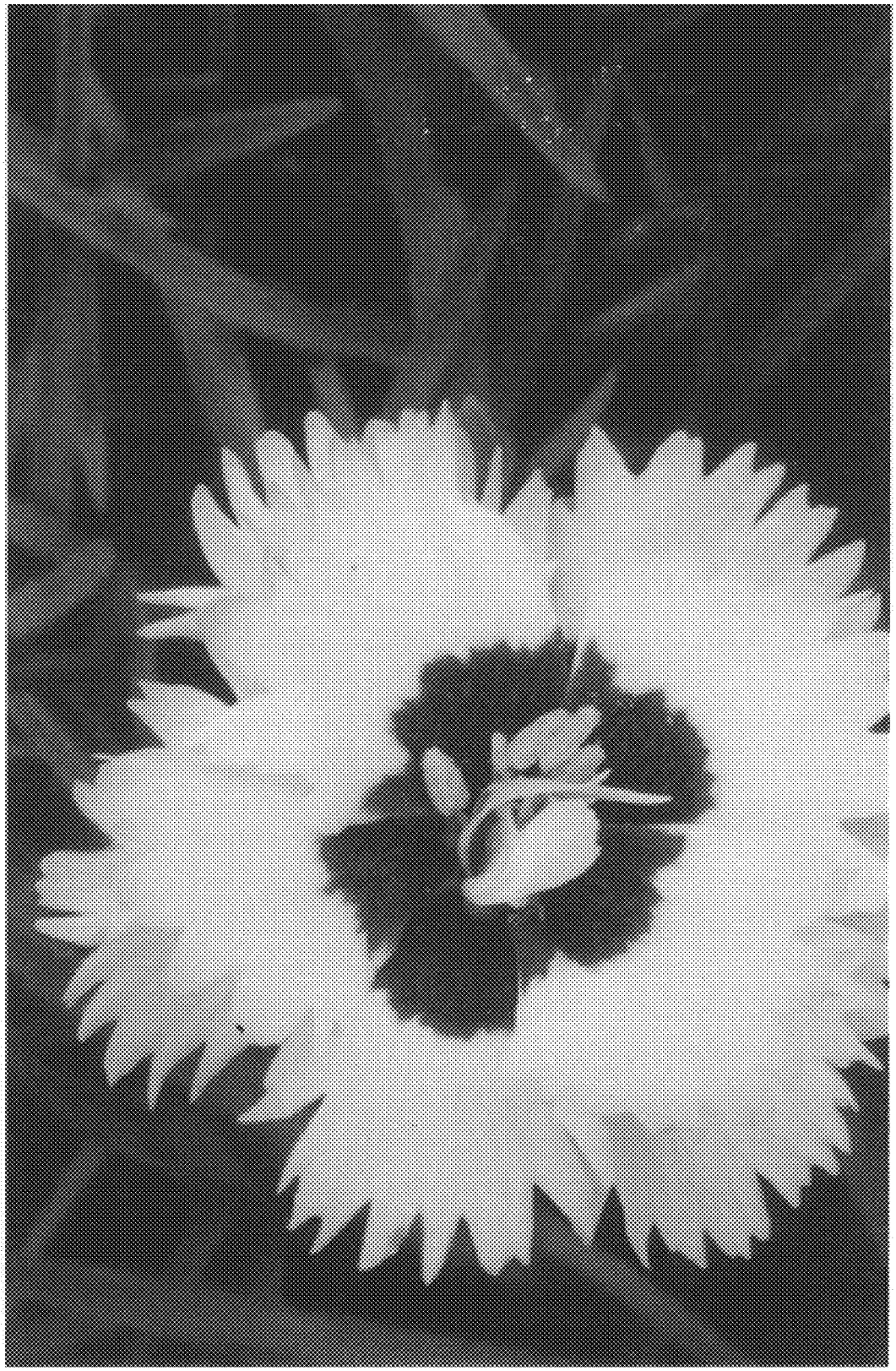

* * * * *